United States Patent
Harrison (10) Patent No.: US 6,636,768 B1
(45) Date of Patent: Oct. 21, 2003

(54) IMPLANTABLE MIRCOPHONE SYSTEM FOR USE WITH COCHLEAR IMPLANT DEVICES

(75) Inventor: William Vanbrooks Harrison, Valencia, CA (US)

(73) Assignee: Advanced Bionics Corporation, Slymar, CA (US)

( * ) Notice: Subject to any disclaimer, the term of this patent is extended or adjusted under 35 U.S.C. 154(b) by 36 days.

(21) Appl. No.: 09/854,420

(22) Filed: May 11, 2001

Related U.S. Application Data (60) Provisional application No. 60/203,706, filed on May 11, 2000.

(51) Int. Cl.[7] ................................................. A61N 1/08
(52) U.S. Cl. ............................................ 607/57; 623/10
(58) Field of Search ................. 181/129; 381/312–316; 607/55–57, 137; 623/10

(56) References Cited

U.S. PATENT DOCUMENTS

| | | | |
|---|---|---|---|
| 3,702,957 A | * 11/1972 | Wolfendale | |
| 4,267,410 A | 5/1981 | Forster et al. | 179/107 |
| 4,428,377 A | 1/1984 | Zollner et al. | 128/419 |
| 4,532,930 A | 8/1985 | Crosby et al. | 128/419 |
| 4,678,991 A | * 7/1987 | Schmidt | 324/207 |
| 5,603,726 A | 2/1997 | Schulman et al. | 607/57 |
| 5,814,095 A | 9/1998 | Muller et al. | 607/57 |
| 5,859,916 A | 1/1999 | Ball et al. | 381/326 |
| 5,999,632 A | 12/1999 | Leysieffer et al. | 381/328 |
| 6,093,144 A | 7/2000 | Jaeger et al. | 600/25 |
| 6,190,305 B1 | * 2/2001 | Ball et al. | 600/25 |
| 6,216,040 B1 | 4/2001 | Harrison | 607/57 |
| 6,342,035 B1 | * 1/2002 | Kroll et al. | 600/25 |

FOREIGN PATENT DOCUMENTS

| WO | WO 97/18689 | 5/1997 |
|---|---|---|
| WO | 0160116 | 8/2001 |

OTHER PUBLICATIONS

US 5,730,699, 3/1998, Adams et al. (withdrawn)

* cited by examiner

*Primary Examiner*—Jeffrey R. Jastrzab
*Assistant Examiner*—Frances P. Oropeza
(74) *Attorney, Agent, or Firm*—Bryant R. Gold (57) ABSTRACT

An implantable microphone system senses "sound" by sensing motion of middle ear components using a linear-variable-differential transformer. The transformer has a movable floating core that is affixed to one or more of the movable middle ear components, such as the tympanic membrane, incus, malleus, stapes, or oval window membrane. Motion of the middle ear component is sensed by applying out-of-phase signals to primary windings of the transformer while monitoring the signal magnetically induced through the movable core on a secondary winding of the transformer. In another embodiment, a capacitor has a movable plate affixed to the movable middle ear component, and motion of the middle ear component is sensed by applying out-of-phase signals to fixed plates of the capacitor.

17 Claims, 4 Drawing Sheets

IMPLANTABLE MIRCOPHONE SYSTEM FOR USE WITH COCHLEAR IMPLANT DEVICES

This application claims the benefit of U.S. Provisional Application Ser. No. 60/203,706, filed May 11, 2000.

BACKGROUND OF THE INVENTION

The present invention relates to an implantable microphone system useable with cochlear implants or implantable hearing aids, and more particularly to an implantable microphone system that uses a highly sensitive motion/position sensor that may be coupled to middle ear structure.

A cochlear implant is an electronic device designed to provide useful hearing and improved communication ability to individuals who are profoundly hearing impaired and unable to achieve speech understanding with hearing aids. Hearing aids (and other types of assistive listening devices) make sounds louder and deliver the amplified sounds to the ear. For individuals with a profound hearing loss, even the most powerful hearing aids may provide little to no benefit.

A profoundly deaf ear is typically one in which the sensory receptors of the inner ear, called hair cells, are damaged or diminished. Making sounds louder or increasing the level of amplification, e.g., through the use of a hearing aid, does not enable such an ear to process sound. In contrast, cochlear implants bypass damaged hair cells and directly stimulate the hearing nerves with electrical current, allowing individuals who are profoundly or totally deaf to receive sound.

In order to better understand how a cochlear implant works, and how the present invention is able to function, it is helpful to have a basic understanding of how the ear normally processes sound. The ear is a remarkable mechanism that consists of three main parts: the outer ear, the middle ear and the inner ear. The outer ear comprises the visible outer portion of the ear and the ear canal. The middle ear includes the eardrum and three tiny bones. The inner ear comprises the fluid-filled snail-shaped cochlea, which contains thousands of tiny hair cells.

When the ear is functioning normally, sound waves travel through the air to the outer ear, which collects the sound and directs it through the ear canal to the middle ear. The sound waves strike the eardrum (tympanic membrane) and cause it to vibrate. This vibration creates a chain reaction in the three tiny bones in the middle ear. These three tiny bones are medically termed the malleus, incus and stapes, but are also commonly referred to as the "hammer", "anvil" and "stirrup". Motion of these bones, in turn, generates movement of the oval window, which in turn causes movement of the fluid contained in the cochlea.

As indicated above, the cochlea is lined with thousands of tiny sensory receptors commonly referred to as hair cells. As the fluid in the cochlea begins to move, the hair cells convert these mechanical vibrations into electrical impulses and send these signals to the hearing nerves. The electrical energy generated in the hearing nerves is sent to the brain and interpreted as "sound".

In individuals with a profound hearing loss, the hair cells are damaged or depleted. In these cases, electrical impulses cannot be generated normally. Without these electrical impulses, the hearing nerves cannot carry messages to the brain, and even the loudest of sounds may not be heard.

Although the hair cells in the cochlea may be damaged, there are usually some surviving hearing nerve fibers. A cochlear implant works by bypassing the damaged hair cells and stimulating the surviving hearing nerve fibers, or ganglion cells, with an electrical signal. The stimulated nerve fibers then carry the electrical signals to the brain, where they are interpreted as sound.

Representative cochlear implant devices are described in U.S. Pat. Nos. 4,267,410; 4,428,377; 4,532,930; and 5,603,726, incorporated herein by reference.

Cochlear implants currently use external microphones placed on the body that pick up sound (sense acoustic pressure waves and convert them to electrical signals) and then transmit the electrical signals to a signal processor for amplification, processing and conversion into an electrical stimulation signal (either current or voltage) that is applied to the surviving acoustic nerves located in the cochlea. Such a microphone is, by design, very sensitive, and in order to be sensitive, is by its nature very fragile. Disadvantageously, the external microphone can be damaged if it becomes wet, is dropped or is exposed to extreme conditions frequently encountered in the external environments. These fragile and sensitive microphones also restrict the user's lifestyle and activities. For example, when a user must wear a microphone, he or she is typically restricted from participation in swimming and other sports, e.g., contact sports, unless the microphone is removed during such activities. If the microphone is removed, however, the user no longer is able to hear. Moreover, many users also find external microphone cosmetically objectionable since they appear out of place and mark the user as "needing assistance".

Middle ear microphones are known in the art. Disadvantageously, however, such prior art middle ear microphones typically require that sensors be attached between moving middle ear structures and stationary parts of the middle ear. This attachment may constrain motion and reduce or modify the performance of these moveable middle ear structures, resulting in an undesirable frequency response and/or distortion in sounds that are perceived. Further, adding too much mass to the ossicle chain or other moving structures of the middle ear may also change the dynamic behavior of the middle ear. What is needed, therefore, relative to a middle ear microphone, or a microphone coupled to middle ear structure, is a microphone that preserves the structure and dynamic performance of the middle ear as much as possible.

An example of an implantable microphone is found in U.S. Pat. No. 5,814,095, incorporated herein by reference. One technique for mounting such a microphone near the ear canal is shown in U.S. Pat. No. 5,999,632. When mounted as disclosed in the 5,999,632 patent, the implantable microphone disclosed in the U.S. Pat. No. 5,814,095 patent is not implanted in the middle ear, but is acoustically coupled to the outer ear.

From the above, it is thus evident that improvements are needed in the way users of a cochlear implant, or other hearing aid systems, sense or hear sounds, and more particularly, it is evident that improvements are needed in the microphones used with such systems, including implantable microphones coupled to middle ear structure.

SUMMARY OF THE INVENTION

The present invention addresses the above and other needs by replacing the external microphone commonly used with cochlear implants or other hearing aid systems with an implantable microphone system. Advantageously, such implantable microphone system detects "sound" by sensing the motion of middle ear components, e.g., by sensing the motion of the ossicles, without seriously degrading the performance of the middle ear components.

In one embodiment, a linear-variable-differential transformer (LVDT) is used within the middle ear to sense very small motion and position. A movable magnetic core of the LVDT is attached to the ossicies or other moving structure within the middle ear in order to measure their relative motion. Advantageously, the movable core need not be attached to any other structure. As the core of the LVDT is displaced from side-to-side by motion of the ossicles (or other movable members within the middle ear), which motion is created by audio signals (sound waves) that impinge upon the tympanic membrane, a modulated signal is induced in the windings of the transformer. This modulated signal has a phase change associated therewith that can readily be detected using conventional detection means. Such detected phase change may then be readily converted into a representation of the audio signal impinging upon the tympanic membrane.

In another embodiment, the movable plate of a movable-plate differential capacitor (MPDC) is attached to the ossicles or other movable structure of the middle ear in order to measure the relative motion thereof. Advantageously, the movable plate of the MPDC need not be attached to any other structure. As the plate of the MPDC is displaced from side-to-side by motion of the ossicles (or other movable members within the middle ear), which motion is created by audio signals (sound waves) that impinge upon the tympanic membrane, a modulated charge or voltage signal is created that is present on the non-moving plates of the MPDC. The modulation of this signal can readily be detected using conventional detection means. Such detected modulation may then be readily converted into a representation of the audio signal impinging upon the tympanic membrane.

In broad terms, the invention may be summarized as an implantable microphone system that includes: (1) a sensor having a movable member for sensing motion of moveable middle ear components, wherein the movable sensor member is adapted to be coupled only to a moving member within the middle ear, without being attached to any other middle ear elements, i.e., so that the movable member "floats" with the movable middle ear member, and wherein the sensor is implantable within the middle ear; and (2) circuit means coupled to the sensor for generating a modulated signal that varies as a function of the relative motion of the movable sensor member. Advantageously, the modulated signal thus functions as a microphone output signal that varies as a function of acoustic sound waves received through the outer ear and impressed upon the movable middle ear components.

In accordance with one aspect of the invention, the surviving tympanic membrane or other middle ear components is/are used as an effective diaphragm for a fully implanted microphone. Even though hearing may be lost, most individuals who are characterized as profoundly deaf still have a fully functioning tympanic membrane and middle ear components. The present invention advantageously relies on the response of such fully functioning tympanic membrane or other middle ear components as incoming acoustic pressure waves are received in the outer ear and funneled into the ear canal. The acoustically induced vibrations in any of these moving components in the middle ear is detected using, in one preferred embodiment, a LVDT transformer having a movable core that is coupled to a moving member of the middle ear, and in another preferred embodiment, a MPDC capacitor having a movable plate coupled to a moving member of the middle ear.

In operation, the the LVDT has three windings and a movable magnetic core. The movable magnetic core is adapted to be coupled only to a movable member of the middle ear, e.g., the ossicle chain. In one embodiment, the movable core may actually replace one or more of the tiny ossicle bones. The LVDT has three groups of windings, L1, L2 and L3, in addition to the movable magnetic core. These windings are not physically connected to the magnetic core, but are magnetically linked thereto. The movable magnetic core is attached to one of the moving structures of the middle ear so that it is positioned approximately equally between coils L1 and L2, which coils function as primary windings of the transformer. The signals impressed on coils L1 and L2 are magnetically coupled, through the movable core, to the third winding L3, which functions as a secondary winding of the transformer. The signal applied to coil L2 is set to be 180 degrees out of phase with the signal applied to coil L1, resulting in the signal induced in coil L3 nominally being zero. However, as the core is displaced from side-to-side because of the motion of the middle ear movable member, more (or less) coupling is provided from coil L1 to coil L3 than is provided from coil L2 to coil L3. The net result is that a modulated signal is provided at coil L3 that has a phase change that can be detected through conventional means and turned into a representation of the audio signal that impinges on the tympanic membrance.

Advantageously, by using the movable core of the LVDT as the moving element, the need for flexing wire connections is eliminated. Also, if desired, the number of connections can be reduced by inverting the connections on coil L2 and connecting them in parallel to the connection to coil L1.

For the embodiment where the MPDC is utilized, the movable plate is coupled or attached to a movable member of the middle ear, and the operation is similar. That is, the MPDC has a first plate P1, a second plate P2, an output plate P4 and a movable plate P3. The capacitance sensed at plate P4 is a function of the spacing between the movable plate P3 and the plates P1 and P2. By applying a signal to plate P2 that is 180 degrees out of phase relative to the signal applied to plate P1, the nominal output sensed at plate P4 is zero. However, as the position of the movable plate P3 varies, as sound impinges upon the tympanic membrane and causes the middle ear members to move, a signal is detectable at the output plate P4 that represents the audio signal impinging upon the tympanic membrane.

The movable core of the LVDT, or the movable plate of the MPDC, can be attached to one of the existing ossicle bones, or to the tympanic membrane or to the oval window. Alternatively, the movable core or movable plate may be built into a prosthetic type of device that is used in a standard stapedectomy procedure, i.e., a procedure where the prosthetic device replaces one or more of the ossicle bones.

Thus, it is seen that the implantable microphone system provided by the invention is directed broadly to systems and methods for detecting relative motion of the functioning middle ear components.

The present invention offers the advantage of an implantable microphone system that uses many of the acoustic properties of the ear that nature provided. That is, because both the outer ear and middle ear components are used, the directional performance for sensing sound is enhanced. Moreover, there may be, for some patients, a natural stapedius response provided by the natural tightening of the tympanic membrane by the stapedius tendon. Further, the location of the device in the middle ear also provides protection from the outside environment as well as a cosmetic enhancement.

The invention may also be characterized as a method of sensing sound using implantable components and generating a microphone signal representative of the sensed sound, which microphone signal is useable by a cochlear implant or other hearing aid device. The method comprises the steps of: (a) implanting a motion sensor in the middle ear, the motion sensor including means for sensing movement of at least one middle ear component; (b) sensing motion of at least one of the moveable middle ear components using the implanted motion sensor; and (c) converting the sensed motion of at least one middle ear component to the microphone signal representative of sensed sound. In one embodiment, the motion sensor comprises a linear-variable-differential transformer (LVDT). In another embodiment, the motion sensor comprises a movable plate differential capacitor (MPDC), or equivalent capacitive element.

It is thus an object of the present invention to provide an implantable microphone that may be used with a cochlear implant or other hearing aid system.

It is a further object of the invention to provide an implantable microphone system that utilizes many of the natural acoustic properties of the ear that nature provided, such as the ability to use the outer ear to collect and direct sound into the ear canal, and the ability to use the functioning middle ear components without interference with the motion of such middle ear components through physical contact therewith.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
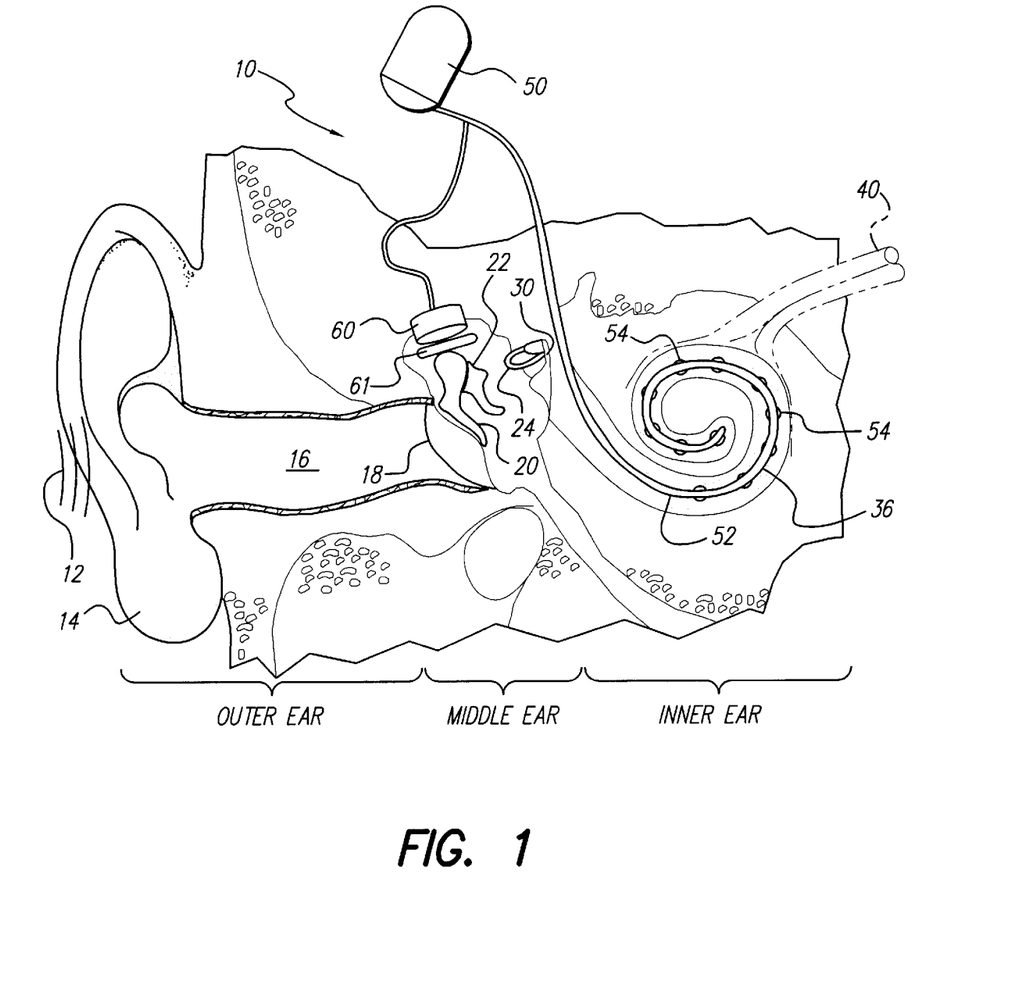
FIG. 1 is a functional schematic diagram of the ear, showing the manner in which an implantable microphone system is made through the use of a sensor implanted within the middle ear.

With reference to FIG. 1, there is shown a functional block diagram of an implantable microphone system 10 in accordance with the present invention. Also schematically shown in FIG. 1 are the major relevant components of the outer, middle and inner ear that typically play a role when using the invention.

The outer ear includes the auricle 14 and the ear canal 16. An acoustic pressure wave, represented in FIG. 1 by the lines 12, is collected by the auricle 14 and funneled into the ear canal 16. At the end of the ear cannel 16 is the "ear drum" 18, or in medical terms, the tympanic membrane 18. In a normal person (a person who is not significantly hearing impaired) the received acoustic wave 12 causes the tympanic membrane 18 to vibrate, which vibration is coupled through three tiny bones, the malleus ("hammer") 20, the incus ("anvil") 22 and the stapes ("stirrup") 24, to the oval window 30. These bones of the middle ear serve to filter and amplify the perceived acoustic wave 12, causing the oval window 30 to articulate, or vibrate, in response to the acoustic wave 12. Vibration of the oval window, in turn, sets up waves of fluid motion within the fluid contained within the snail-shaped cochlea 36. Such fluid motion, in turn, activates tiny hair cells (not shown in FIG. 1) that line the inside of the cochlea 36. Activation of the hair cells causes appropriate nerve impulses to be transferred through the spiral ganglion 40 to the brain, where they are perceived as sound.

For many individuals who suffer from profound deafness, the hair cells have been damaged to the point where it is not possible to activate them. Hence, an implantable cochlear stimulator (ICS) 50 may be implanted near the ear, and an electrode array 52, having a plurality of spaced apart electrodes 54 thereon, is inserted into the cochlea 36. As explained previously, such ICS 50, when used in a conventional manner, e.g., as taught in the referenced patents, is coupled to an external microphone that senses sounds. Such coupling may occur through various means, but is usually achieved through an inductive coupling link with an external head piece, connected to a wearable processor. Such link also provides a way for power to be coupled into the implanted ICS 50. The sounds sensed by the external microphone are processed and converted to appropriate electrical stimuli that are selectively applied to the electrode contacts 54 of the electrode array 52. Such electrical stimuli bypass the defective hair cells and directly activate the nerves within the of the spiral ganglion, causing nerve impulses to be transferred to the brain, where they may be perceived as sound.

In contrast to the conventional method of using an ICS as explained in the previous paragraph, the present invention utilizes an implantable sensor 60, 61 coupled to an implantable cochlear stimulator (ICS) 50, as shown in FIG. 1, as an implantable microphone system 10. As seen in FIG. 1, the sensor has a stationary part 60 and a movable part 61 that function together, i.e., elements or components in the stationary part 60 sense motion of the movable part 61. The stationary part 60 is implanted so that at least a portion of it resides within the middle ear, but so that it does not physically come in contact with the moving elements that reside within the middle ear. That is, the sensor 60 does not physically come in contact with the tympanic membrane 18, the malleus 20, the incus 22, the stapes 24, or the oval window 30. In contrast, the movable part 61 is implanted within the middle ear so that it is coupled, or attached to, one of the moving elements within the middle ear, e.g., so that it is coupled to or attached to the tympanic membrane 18, the malleus 20, the incus 22, the stapes 24, or the oval window 30. Significantly, the movable part 61 is not in contact with any non-moving elements, or the walls, of the middle ear. As a result, the movable part 61 is able to "float", or freely move with, the movable middle ear component to which it is coupled. Thus, as the functioning middle ear components move as a function of acoustic sound waves 12 collected through the outer ear, the movable part 61 of the sensor 60 also moves as a function of the acoustic sound waves 12.

For the embodiment shown in FIG. 1, where the stationary part 60 of the implantable microphone sensor 10 is electrically connected directly to the ICS 50, it is understood that the ICS 50 includes the necessary signal processing circuitry, e.g., speech processing circuitry as is known in the art, for converting the signals generated by the sensor 10 to appropriate signals needed to stimulate the nerve within the inner ear, e.g., the nerves within the spiral ganglion.

The sensor 60, with movable member 61 coupled to a movable middle ear component, may take various forms. In one embodiment, schematically depicted in FIG. 2A, a linear-variable-differential transformer (LVDT) 59 is used. The LVDT 59 has three windings L1, L2 and L3 and a movable magnetic core 58. The movable magnetic core 58 is adapted to be coupled only to a movable member of the middle ear, e.g., to one of the bones of the ossicle chain. In an alternate embodiment, the movable core may actually replace one or more of the tiny ossicle bones. The windings or coils L1, L2, and L3 are not physically connected to the magnetic core 58, but are magnetically linked thereto through the transformer core. The movable magnetic core 58 is attached to one of the moving structures of the middle ear so that it is positioned approximately equally between coils L1 and L2, which coils function as primary windings of the transformer. The signals impressed on coils L1 and L2 are magnetically coupled, through the movable core, to the third winding L3, which functions as a secondary winding of the transformer. The signal applied to coil L2 is set to be 180 degrees out of phase from the signal applied to coil L1. For example, the signal applied to coil L1 may be sin $\omega_o t$, and the signal applied to coil L2 may be $-\sin \omega_o t$, where $\omega_o$ represents a selected carrier frequency. With equal but opposite-phased signals applied to coils L1 and L2, the signal induced in coil L3 will be zero. However, as the core 58 is displaced from side-to-side because of the motion of the middle ear movable member, more (or less) coupling is provided from coil L1 to coil L3 than is provided from coil L2 to coil L3. The net result is that a modulated signal is provided at coil L3 that has a phase change that can be detected through conventional means and turned into a representation of the audio signal that impinges on the tympanic membrance.

Figure 2A:
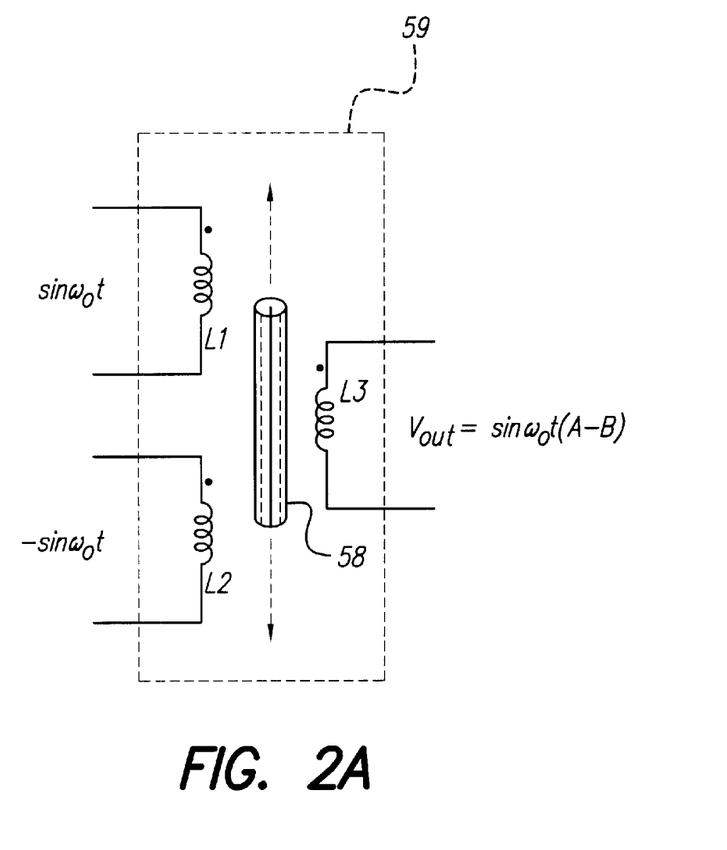
FIG. 2A is a schematic diagram of a liner-variable-differential transformer (LVDT) having a movable magnetic core, which LVDT may be used, in one embodiment of the invention, as the sensor of FIG. 1.
Figure 2B:
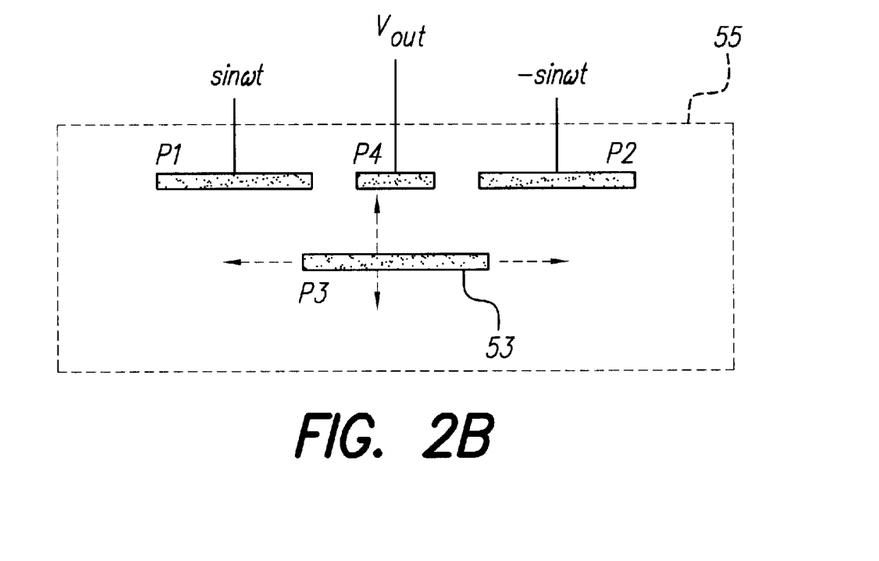
FIG. 2B is a schematic diagram of a movable-plate-differential capacitor (MPDC), having a movable plate P3, which MPDC may be used, in another embodiment of the invention, as the sensor of FIG. 1.

In another embodiment, schematically depicted in FIG. 2B, the sensor 60 with movable member 61 takes the form of a movable plate differential capacitor (MPDC) 55. The MPDC 55 has a first plate P1, a second plate P2, an output plate P4 and a movable plate P3. The movable plate P3 is affixed to one of the moving elements of the middle ear, e.g., to one of the ossicle bones. The capacitance sensed at plate P4 is a function of the spacing between the movable plate P3 and the plates P1, P2 and P4. By applying a signal to plate P2 that is 180 degrees out of phase relative to the signal applied to plate P1, the nominal output sensed at plate P4 is zero. However, as the position of the movable plate P3 varies, as sound impinges upon the tympanic membrane and causes the middle ear member to which the movable plate P3 is affixed to move, a signal is detectable at the output plate P4 that represents the audio signal impinging upon the tympanic membrane.

It is noted that the movable core 58 of the LVDT 59, or the movable plate P3 of the MPDC 55, can be attached to one or more of the existing ossicle bones 20, 22, or 24, to the tympanic membrane 18, or to the oval window 30. Alternatively, the movable core or movable plate may be built into a prosthetic type of device that is used in a standard stapedectomy procedure, i.e., a procedure where the prosthetic device replaces one or more of the ossicle bones.

There are several approaches that may be used in accordance with the present invention in order to implement the basic concept of the invention as described above. The feature common to all approaches or implementations of the invention is to use an active rather then a passive approach to produce an implantable microphone that uses the moving elements of the middle ear. In fact, almost any dynamic parameter that changes in response to acoustic pressure on the tympanic membrane may be used to produce an electrical signal that represents this pressure. These parameters can include physical motion, pressure variation in water, pressure variation in air, etc.

Figure 3:
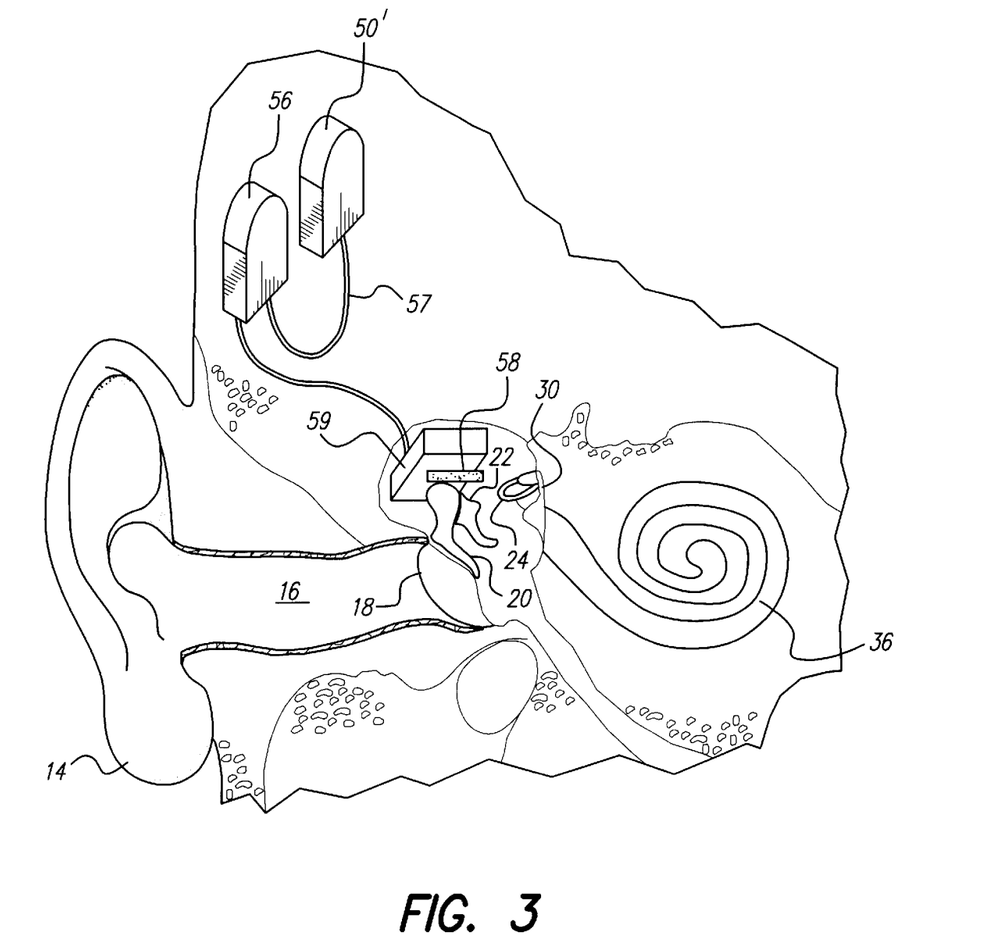
FIG.3 shows one embodiment of the invention that includes the use of a linear-variable-differential transformer (LVDT)

One implementation of a microphone system 10 using a linear-variable-differential transformer (LVTD) 59 is illustrated in FIG. 3. The embodiment of the invention shown in FIG. 3 includes the use of a LVDT 59 having a movable core 58 affixed to the incus 22. As seen in FIG. 3, an implanted ICS 50' is coupled to an implantable speech processor and power module 56 via a suitable connecting cable 57. The LVDT 59 is electrically connected to the implanted speech processor and power module 56. Appropriate circuitry is provided within the module 56 to apply signals of opposite phases to the two primary windings L1 and L2 that are included within the LVDT 59 (see FIG. 2A). Additional circuitry is provided within the module 56 to sense and monitor the output signal, $V_{OUT}$, present at the secondary winding of the LVDT 59. The output signal represents the relative motion of the incus 22, and as such, provides an electrical signal indicative of the acoustic sound that impinges upon the tympanic membrane 18.

In FIG. 3, the movable core 58 is affixed to the incus 22. However, it is noted that other middle ear components that move as acoustic sound is sensed could also carry the floating movable core 58.

Figure 4:
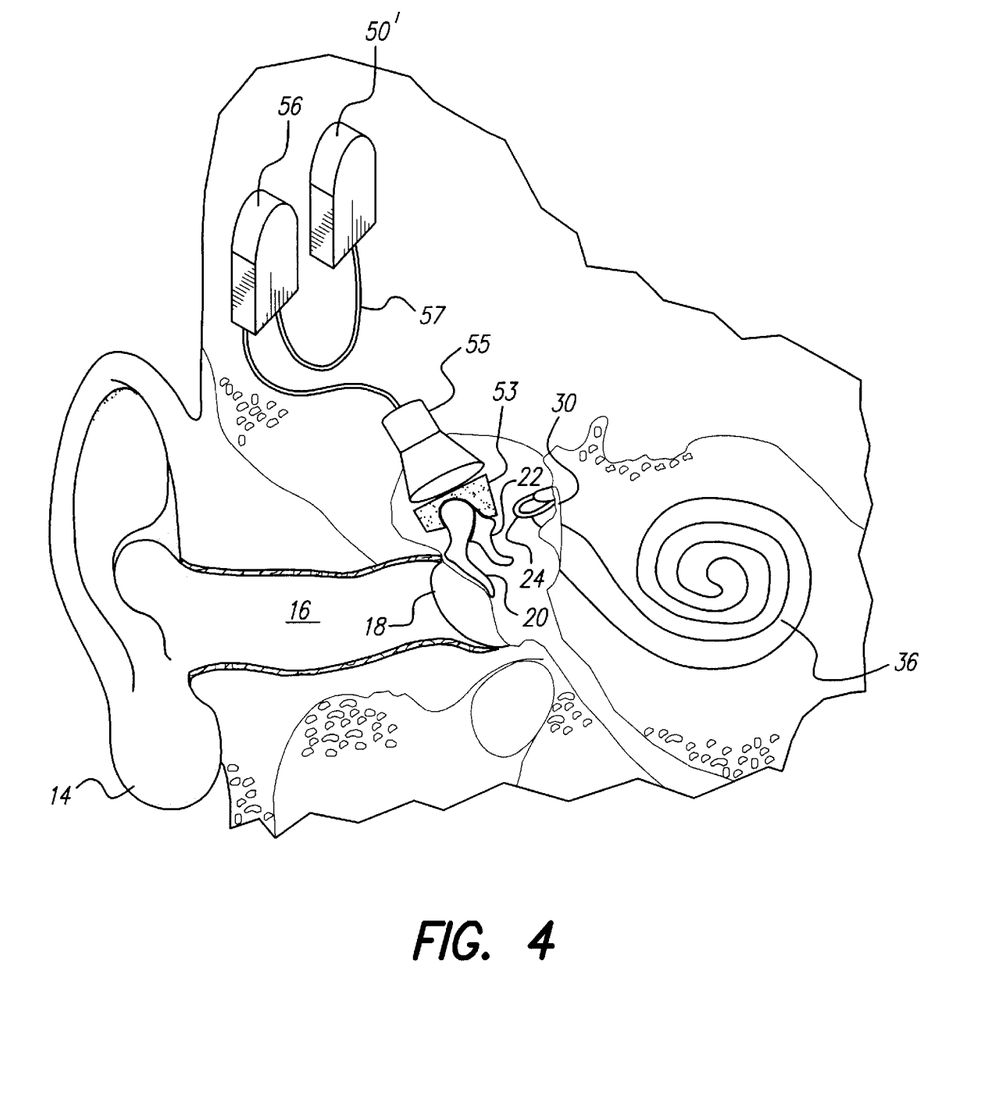
FIG. 4 illustrates another embodiment of the invention that uses a moveable-plate-differential capacitor (MPDC).

As seen in FIG. 4, a movable plate differential capacitor (MPDC) 55 is mounted in the middle ear. As seen in FIG. 4, an implanted ICS 50' is coupled to an implantable speech processor/power module 56 via a suitable connecting cable 57. As explained previously in connection with FIG. 2B, the MPDC 55 includes fixed plates and a movable plate 53. The movable plate 53 is affixed to, e.g., the malleus 20 and the incus 22. In operation; as acoustic sound is collected in the outer ear and causes the tympanic membrane 18 to vibrate, both the malleus 20 and incus 22 also vibrate, or move. Such movement is coupled to the movable plate 53 of the MPDC 55. As the plate 53 moves, such movement is electrically detectable by monitoring the signal present on the output plate P4 (see FIG. 2B) of the MPDC.

As described above, it is thus seen that the present invention provides an implantable microphone that may be used with a cochlear implant or other hearing aid system. More particularly, it is seen that the invention provides an implantable microphone system that advantageously utilizes many of the natural acoustic properties of the ear, such as its ability to use the outer ear to collect and direct sound into the ear canal, and its functioning middle ear components, to generate an electrical output signal representative of the sensed sound.

While the invention herein disclosed has been described by means of specific embodiments and applications thereof, numerous modifications and variations could be made thereto by those skilled in the art without departing from the scope of the invention set forth in the claims.

What is claimed is:

1. An implantable microphone and cochlea stimulation system comprising:
 a sensor for sensing motion of middle ear components, the sensor having a first part and a second part, wherein the first part floats and is not in physical contact with the second part, wherein the first part is adapted to be affixed to a movable middle ear component, wherein the sensor is implantable within the middle ear;
 processing means coupled to the sensor for generating an electrical signal representative of relative motion between the first part and second part of the sensor, wherein the electrical signal comprises a microphone output signal that varies as a function of movable middle ear components; and
 an implantable cochlear stimulator responsive to the microphone output signal. the implantable cochlear stimulator comprising signal processing means for converting the microphone output signal to stimulus signals adapted to stimulate nerves within the inner ear. and an electrode array having a plurality of spaced-apart electrodes thereon through which the stimulus signals are applied to the nerves of the inner ear.

2. The system of claim 1 wherein the sensor comprises a linear-variable-differential transformer (LVDT).

3. The system of claim 2 wherein the LVDT has a movable magnetic core and first, second, and third windings, and wherein the movable magnetic core comprises the first part of the sensor that is adapted to be affixed to the movable middle ear component, and wherein the first, second and third windings comprise, in combination, the second part of the sensor.

4. The system of claim 3 wherein the processing means includes circuitry that generates carrier signals of opposite phase that are applied to the first and second windings, and wherein a signal magnetically induced in the third winding represents the relative motion between the first part and the second part of the sensor.

5. The microphone system of claim 3 wherein the first and second windings of the LVDT are connected in parallel with opposite winding polarities.

6. The implantable microphone system of claim 1 wherein the sensor comprises a movable plate differential capacitor (MPDC).

7. The system of claim 6 wherein the MPDC has a movable plate and fixed first, second, and third plates, and wherein the movable plate comprises the first part of the sensor that is adapted to be affixed to the movable middle ear component, and wherein the first, second and third plates comprise, in combination, the second part of the sensor.

8. An implantable microphone and cochlea stimulation system comprising:
 a linear-variable-differential transformer (LVDT) that senses motion of middle ear components, the LVDT having a first part and a second part, wherein the first part floats and is not in physical contact with the second part, wherein the first part is adapted to be affixed to a movable middle ear component, wherein the LVDT is implantable within the middle ear;
 processing means coupled to the LVDT for generating an electrical signal representative of relative motion between the first part and second part of the LVDT, wherein the electrical signal comprises a microphone output signal that varies as a function of movable middle ear components, and
 an implantable cochlear stimulator responsive to the microphone output signal, the implantable cochlear stimulator comprising signal grocessing means for converting the microphone output signal to stimulus signals adapted to stimulate nerves within the inner ear. and an electrode array having a plurality of spaced-apart electrodes thereon through which the stimulus signals are applied to the nerves of the inner ear.

9. The system of claim 8 wherein the LVDT has a movable magnetic core and first, second, and third windings, and wherein the movable magnetic core comprises the first part of the LVDT that is adapted to be affixed to the movable middle ear component, and wherein the first, second and third windings comprise, in combination, the second part of the LVDT.

10. The system of claim 9 wherein the processing means includes circuitry that generates carrier signals of opposite phase that are applied to the first and second windings, and wherein a signal magnetically induced in the third winding represents the relative motion between the first part and the second part of the sensor.

11. The system of claim 9 wherein the first and second windings of the LVDT are connected in parallel with opposite winding polarities.

12. A method of sensing sound using implantable components and generating a microphone signal representative of the sensed sound, which microphone signal is useable by a cochlear implant device, the method comprising:
 (a) implanting a motion sensor in the middle ear, the motion sensor including means for sensing movement of at least one middle ear component, the motion sensor having a first part and a second part, wherein the first part floats and is not in physical contact with the second part, wherein the first part is adapted to be affixed to a moveable middle ear component;
 (b) sensing motion of at least one of the moveable middle ear components using the implanted motion sensor; the motion of the middle ear component resulting in relative motion between the first part and the second part of the sensor;
 (c) converting the sensed motion of the at least one middle ear component to the microphone signal representative of sensed sound;
 (d) applying the microphone signal to the cochlear implant device; and
 (e) generating cochlea stimulus signals within the cochlear implant device in response to the microphone signal; and
 (f) applying the cochlea stimulus signals to nerves within the cochlea to Provide the perception of sound.

13. The method of claim 12 wherein sensing motion of a moveable middle ear component comprises affixing a movable core of a linear-variable-differential transformer (LVDT) to the moveable middle ear component, and applying appropriate signals to windings of the LVDT that allow relative motion of the movable core to be detected.

14. The method of claim 12 wherein sensing motion of a moveable middle ear component comprises affixing a moveable plate of a movable plate differential capacitor (MPDC) to the moveable middle ear component, and applying appropriate signals to fixed plates of the MPDC that allow relative motion of the movable plate to be detected.

15. An implantable microphone and cochlear implant system adapted for use by a patient having a functioning tympanic membrane and middle ear components, outer ear and ear canal, comprising:

an implantable microphone adapted to sense motion of the tympanic membrane as incoming acoustic pressure waves are received in the outer ear and funneled into the ear canal;

wherein the implantable microphone includes (a) sensing means for sensing motion of middle ear components coupled to the tympanic membrane, wherein the sensing means comprises a first part and a second part, wherein the first part floats and is not in physical contact with the second part, and wherein the first part is adapted to be coupled to a movable middle ear component, and (b) processing means responsive to the sensing means for generating an electrical signal representative of relative motion between the first part and second part of the sensing means, wherein the electrical signal comprises a microphone output signal that varies as a function of movable middle ear components; and an implantable cochlear stimulator responsive to the microphone output signal, the implantable cochlear stimulator having (a) signal processing means for converting the microphone output signal to stimulus signals adapted to stimulate nerves within the inner ear, and (b) an electrode array having a plurality of spaced-apart electrodes thereon through which the stimulus signals are applied to the nerves of the inner ear.

16. The implantable microphone and cochlear implant system of claim 15 wherein the sensing means comprises a linear-variable-differential transformer (LVDT) having a movable magnetic core and first, second, and third windings, and wherein the movable magnetic core comprises the first part of the sensing means adapted to be affixed to the movable middle ear component, and wherein the first, second and third windings comprise, in combination, the second part of the sensing means.

17. The implantable microphone and cochlear implant system of claim 15 wherein the sensing means comprises a movable plate differential capacitor (MPDC) having a movable plate and fixed first, second, and third plates, and wherein the movable plate comprises the first part of the sensing means that is adapted to be affixed to the movable middle ear component, and wherein the first, second and third plates comprise, in combination, the second part of the sensing means.

* * * * *